United States Patent [19]
Landry et al.

[11] Patent Number: 6,080,736
[45] Date of Patent: Jun. 27, 2000

[54] METHODS AND COMPOSITIONS FOR TREATING AND PREVENTING ANXIETY AND ANXIETY DISORDERS USING OPTICALLY PURE (R) TOFISOPAM

[75] Inventors: Donald W. Landry; Donald F. Klein, both of New York, N.Y.

[73] Assignee: Janus Pharmaceuticals, Inc., New York, N.Y.

[21] Appl. No.: 09/429,503

[22] Filed: Oct. 27, 1999

Related U.S. Application Data

[60] Provisional application No. 60/105,803, Oct. 27, 1998.
[51] Int. Cl.[7] ............................................... A61K 31/5513
[52] U.S. Cl. ............................................................ 514/221

[56] References Cited

U.S. PATENT DOCUMENTS

| | | | |
|---|---|---|---|
| 3,736,315 | 5/1973 | Korosi et al. | 260/239 |
| 4,423,044 | 12/1983 | Korosi et al. | 514/221 |

OTHER PUBLICATIONS

E. Fogassy et al., (1984) "Studies on the Properties and Structure of Optically Active 1–(3, 4–Dimethoxyphenyl)–4–Methyl–5–Ethyl–7, 8–Dimethoxy–5H–2,3–Benzodiazepine (Tofizopam)," *Bio–Organic Heterocycles*, van der Plas, H.C., Otvos L., and Simonyi, M., eds., pp. 229–233.

K. Imre et al., (1993) "A Tofizopam (Grandaxin®) Farmakokinetikaja es Metabolizmusa," *Acta Pharmaccutica Hungarica* 63:83–90.

P. Lujza, (1993) "A Tofizopam (Grandaxin®) Farmakologiai Hatasai," *Acta Pharmaccutica Hungarica* 63:79–82.

K. Maier et al., (1984) "The Effect of Tofisopam on Psychic Performance in Persons With More Than Average Anxiety: A Controlled Experimental Trial," *Current Therapeutic Research* 35(4):541–548.

F. Pal, (1993) "A Grandaxin® Gyógyszertechnológiája," *Acta Pharmaceutica Hungarica* 63:67–78.

L. Petocz et al., (1975) "The Main Pharmacological Characteristics of Grandaxin (Tofizopam, EGYT–341)," *Therp. Hungar.* 23:134–138.

M. Simonyi et al., (1993) "Stereoselective Binding of a 2,3–Benzodiazepine to Human Serum Albumin," *Biochemical Pharmacology* 32(12):1917–1920.

R. Sladkà et al., (1979) "A Placebo–controlled Clinical Trial With Tofizopam in the Treatment of Anxiety Neurosis," *Ther. Hungar.* 27:176–180.

G. Toth et al., (1983) "Racematspaltung von (±)–5–Athyl–1–(3,4–dimethoxyphenyl)–6, 7–dimethoxy–4–methyl–5H–2,3–benzodiazepin und anomales chiroptisches Verhalten der Enantiomeren (1)," *J. Heterocyclic Chem.* 20:709–713.

G. Várady et al., (1975) "The Clinical Evaluation of Grandaxin Used in the Treatment of Outpatients (A Multicentric Study)," *Therap. Hungar.* 23:153–158.

J. Visy et al., (1989) "The Role of Configuration and Conformation in the Binding of 2,3–Benzodiazepines to Human Serum Albumin," *Chirality* 1:271–275.

*Primary Examiner*—Raymond Henley, III
*Attorney, Agent, or Firm*—Fish & Neave; James F. Haley, Jr.; Elinor K. Shin

[57] ABSTRACT

Methods are disclosed utilizing the R enantiomer of tofisopam. This compound is useful in the treatment or prevention of anxiety or anxiety disorders while substantially reducing adverse effects associated with racemic tofisopam.

37 Claims, 3 Drawing Sheets

METHODS AND COMPOSITIONS FOR TREATING AND PREVENTING ANXIETY AND ANXIETY DISORDERS USING OPTICALLY PURE (R) TOFISOPAM

This is an application that claims priority under 35USC119(e) from provisional application Ser. No. 60/105,803 filed Oct. 27, 1998.

1. FIELD OF THE INVENTION

This invention relates to methods and pharmaceutical compositions for treating and preventing anxiety and anxiety disorders using optically pure tofisopam.

2. BACKGROUND OF THE INVENTION

2.1 Chirality in Pharmacology

The concept of chirality is basic to organic and biochemistry and has become a significant factor in determining the actions of a pharmacologic agent. An atom, particularly a carbon atom, is said to be chiral or stereogenic when it is bound to four different atoms or groups in a tetrahedral arrangement. All four atoms or groups must be different in order to make the central atom a chiral center. The importance of this is that such an arrangement can not be superimposed on its mirror image by any rotation of bonds or positioning of the molecule. The two molecules are isomers, that is they have the same empirical formula, but they are not identical and short of breaking and remaking bonds they can not be made identical.

Molecules that differ in the spatial arrangement of their atoms but have the same points of attachments are called stereoisomers. Enantiomers are a subgroup of stereoisomers that are nonsuperimposable mirror images. All molecules that contain stereogenic or chiral centers must have enantiomers. If a molecule can be superimposed on its mirror image by rotation or any motion other than bond making and breaking then they are identical and not enantiomers. A molecule that has more than one chiral center may generate multiple stereoisomers and these are called diastereomers.

Enantiomers are named according to a convention which assigns absolute descriptors R or S to the two possible arrangements of groups around a chiral center. Cahn R. S., Ingold C. R., Prelog V. *Angew. Chem.* (Int Ed.), 5, 385–415 (1966). Enantiomers have similar or identical physiochemical properties. However, they differ in their ability to rotate the plane of plane-polarized light while in solution. Enantiomers will rotate the plane of the light in equal amounts but in opposite directions and are therefore referred to as optical isomers. The ability to rotate the plane of polarized light is often used in the designation of the enantiomer. If the isomer rotates the plane of plane polarized light to the right it is dextrorotatory indicated by a (+) before the name of the compound. The isomer that rotates light to the left is termed levorotatory, indicated by a (−) prefix. The ability of an isomer to rotate the plane of light gives information about the physical property of the material but it does not give information concerning the 3-dimensional spatial arrangement or absolute configuration of the molecule as indicated by prefixes R and S. This complete name of an isomer includes (+) or (−) to indicate its optical properties and an R or S to indicate the molecules absolute configuration.

The variation of absolute configuration embodied in stereoisomers and enantiomers is of profound importance in nature. This is shown by the normal predominance of one enantiomer over another in naturally occurring molecules, e.g., L-amino acid, D-glucose, L-peptides, D-ribonucleotides. In contrast, synthetically made chemicals when made from achiral precursors generally are racemates or roughly equal mixtures of both enantiomers.

This has historically been true of the majority of drugs used to treat human disease which, for the most part, have been manufactured and used therapeutically in their racemic form. It has been calculated that 25% of all drugs on the markets today are chiral molecules and that approximately 80% of these are used as racemates. Lehmann, F. P. A. (1986), *Trends Pharmacol. Sci.,* 7, 281–285.

For some therapeutic agents, chirality may not be important. However, until recently little was known about the effect of enantiomeric differences or stereoselectivity on the pharmacokinetics or pharmacodynamics of drugs. Over the past 10–15 years, there has been increased interest in pharmaceutical stereochemistry. It is now known that enantiomers of a given drug may have markedly different properties in a biological system. These different actions may be due to pharmacokinetic differences, such as effect on protein binding, storage, transport, metabolism, or clearance. Enantiomers may also show differential pharmacodynamic activity and show stereoselectivity in the manner in which they bind to and activate receptors. This selectivity should be expected in drug receptor interactions since many of the natural ligands are themselves chiral, e.g., neurotransmitters, hormones, endogenous peptides, etc. In addition, stereoisomers present as components of racemic mixtures may interact with each other in complex and poorly understood ways.

The recent increase in interest in and attention to pharmaceutical stereochemistry has occurred both because of an increased understanding of the unique properties of enantiomers and because there have been many developments in assymetric synthesis and chiral separation technology. New synthesis techniques have been developed which use chiral starting material or chiral reagents or catalysts which promote enantioselective synthesis. Large scale chromatographic recrystalization techniques and enzymatic reactions have now allowed pharmaceutical companies to produce single enantiomers on a large scale in a cost effective manner.

The effect of chirality on drug action is complex and may involve any or all systems in the body which are capable of reacting to a chiral molecule in an asymmetric or enantioselective manner.

Any active process can be expected to show enantiomeric selectivity or specificity. An active process may involve receptor interaction, enzyme action or binding specificity. In practice, the processes which may involve enantioselectivity include absorption, distribution including protein and tissue binding, storage and transport, metabolism, biliary and renal clearance and receptor binding and activation. Any one of these active processes alone or in combination may affect the therapeutic actions of a stereoisomer in vivo.

2.2 Enantioselectivity in Pharmacokinetics

Enantioselective absorption of a drug may occur if there is (a) active absorption; (b) specific metabolism in gut or gut wall; (c) solubility differences; (d) enantioselective biliary excretion followed by reabsorption or (e) pharmacological activity differences.

Enantioselective active absorption is well known for the naturally occurring isomers such as L-amino acids, D-glucose, etc. The enantioselective amino acid pump will also preferentially transport drugs that are structurally similar such as L-dopa. Wade et al. (1973), *Nature,* 242, 463–465. Such selective active absorption also occurs in the case of L-methotrexate and L-cephalexin, the latter being carried by the enantioselective dipeptide transport system. Tamai et al. (1988), *J. Pharm. Pharmacol.,* 40, 320–324.

Enantioselective gut metabolism may occur with certain drugs. Borgstrom et al. (1989), *Br. J. Clin. Pharmacol.,* 27,49–56. Solubility differences between enantiomers are rare but can cause differential absorption, for example; racemic thalidomide is ten times less soluble than its separate isomers affecting its absorption from the gut. Hague et al. (1988), *Br. J. Clin. Pharmacol.,* 26, 623P.

The degree to which drugs are bound to human serum albumin (HSA) or α-1-acid glycoprotein (AAG) can profoundly affect their pharmacokinetics. The unbound fraction of the drug largely determine the activity and clearance of a drug. However, when binding differences are large there may be changes in the volume of distribution, maximum and minimum unbound levels at steady state, time to reach steady state and total renal clearance.

In general, binding of drugs to either HSA (acidic drugs) or AAG (basic drugs) is not enantioselective but some important exceptions exist. Most drugs bind to HSA at either the warfarin site (site I) or the benzodiazepine and indole site (site II). L-Tryptophan was found to have an affinity for site II of HSA about 100 times that of the D-enantiomer. McMenamy et al. (1958), *J. Biol. Chem.,* 233:1436–37. D-Oxazepam has 40 times the affinity for site II of HSA compared to the L-enantiomer. Muller W E, Wollert U (1975), *Mol. Pharmacol.,* 11:52–60. Other chiral benzodiazepine derivatives, including tofisopam, have also shown similar enantioselective binding to site II of HSA. Alebic-Kolbah et al. (1979), *Biochem. Pharmacol.,* 28:2457–64. Simongi M, Fitos 1. (1983), *Biochem. Pharmacol.,* 32:1917–20.

Binding of basic drugs to α-1-acid glycoprotein (AAG) has also been shown to be enantioselective for propranolol, Albani et. al. (1984), 18:244–46; Disopyramide, Giacormini et al. (1986), *J. Pharmacol. Biopharm.,* 14:325–56; Verapamil, Eichelbaum et al. (1984), *Br. J. Clin. Pharmacol.,* 17:450–8 and Methadone, Romach et al. (1981), *Clin. Pharmacol., Ther.* 29:211–17.

Enantioselective plasma protein binding may not cause as significant an effect on the pharmacologic activity of a drug as stereoselective interaction between enantiomers and receptors. However, selective binding will affect the ratio of total to free drug concentration and enantiomers may displace one another leading to kinetic interactions as has been found for ibuprofen. Lee et al. (1985), *Br. J. Clin. Pharmacol.,* 19:669–674.

The extent of tissue binding of a drug is dependent primarily on lipid solubility and plasma protein binding with lipid solubility being the most important factor. Enantiomers generally have similar lipid solubility so enantioselectivity in tissue uptake is likely to be small unless a specific uptake process exists. This has been shown for the S (−) enantiomers of propranolol and timolol which are specifically taken up by β-receptors and which are more highly bound to cardiac tissue than their antipodes. Kawashima et al. (1976), *J. Pharmacol., Exp. Ther.* 196, 517520, Tocco et al. (1976), *Drug Metab. Discos.* 4, 323–329.

The most significant enantioselective process in drug disposition is enantioselective metabolism. It has been estimated that 75% of all chiral drugs show enantioselective metabolism to some degree. Cambell O. B. (1990), *Eur. J. Drug Metab. Pharmacokinet.,* 15:109–125. The mechanism may involve both an initial recognition binding step and a difference in subsequent rate of activation of the enzyme once bound. Testa B. (1989), *Chirality,* 1, 7–9.

Evidence exists for stereoselectivity in hepatic metabolism of numerous drugs. Enantioselective first pass metabolism may produce substantial differences in plasma concentrations between the oral and intravenous routes of administration. Testa B, Jenner P, *Concepts in Drug Metabolism New York;* Marcel Dekker, 1980:55–176; Echizen et al. (1985), *Am. Heart J.,* 109:210–217.

This enantioselectivity in first-pass metabolism has great clinical significance. Based only on plasma concentration, racemic verapamil is far more potent in terms of prolongation of PR-interval after intravenous than after oral administration. At the same "total" drug plasma concentration the dose response curve shifts to the right following oral administration as compared to intravenous administration. The S-enantiomer is between 2.5 and 20-fold more potent than R-verapamil in causing vasodilation, negative inotropic effect, retardation of atrioventricular conduction and chronotropic effect. Eichelbaum, M. *Biochem. Pharmacol.* 1988:37:93–6. The enantioselective first pass metabolism of the more potent and more toxic enantiomer results in a 2.5 fold higher concentration of S-verapamil after intravenous as compared to oral administration when total plasma drug concentrations are equal.

Numerous enzymes involved in metabolic clearance have shown enantioselective action. This includes mixed-function oxidase, epoxide hydrolases, esterases, glutathione transferases, glucuronyl transferases, tyrosine hydroxylase and dopa decarboxylase. Metabolism of warfarin is highly enantioselective and the drug's enantiomers are metabolized by two different metabolic routes and by different metabolic enzymes. The S-enantiomer is primarily metabolized by oxidation through ring hydroxylation by cytochrome P-450IIC9 to form 7-hydroxy S-warfarin. R-warfarin, by contrast, is metabolized by oxidation by cytochrome P-450IIIA4 to 6-hydroxy-R-warfarin and by reduction of the ketone functional group to form R,S warfarin alcohols. Rettie et al. (1992) *Chem Res Toxicol* 5:54–59; Lewis R J, Trager W F (1970), *J. Clin. Invest.,* 49:907–13.

This is the kind of radical difference in the way the enantiomers of a drug are handled by the body that has prompted investigators to make statements such as "Warfarin enantiomers should be treated as two drugs". Hignite et al. (1980), *Clin. Pharmacol. Ther.,* 28, 99.

Biliary excretion has an active transport component which is different for acids and bases and so should be enantioselective.

Renal clearance of a drug combines both active and passive processes which include glomerular filtration, passive reabsorption, active secretion and active reabsorption and renal metabolism. Tubular secretion and active reabsorption both involve saturable carrier mediated processes which are potentially enantioselective.

2.3 Enantioselectivity in Pharmacodynamics

The absolute configuration of an asymmetric drug molecule may have a profound effect on the drug interaction with a receptor. This has been known since the greater potency of (−) hyoscyamine over its (+) enantiomer was shown in the early part of this century. Cushing A R. *Biological relations of optically isomeric substances,* London. Bailliere, Tendall and Cox, 1926. Less than a decade later a simple but useful model was proposed to explain the differences in pharmacodynamic activity between enantiomers. Easson L H, Stedman, E. (1933) *Biochem. J.* 27, 1257–66. This model proposes that the more active enantiomer is able to interact with the receptor at three points while the less active isomer is only able to interact at two sites. This model is overly simplistic in that it fails to take into account the conformational flexibility of both the drug and receptor macromolecules.

The enantiomer with the higher receptor affinity or activity is termed the eutomer while the one with the lower activity is termed the distomer. The ratio of affinity or activity of the two enantiomers is a measure of the enantioselectivity of the system and is called the eudismic ratio.

The difference in receptor affinity or activity between two enantiomers may be so profound that the two isomers are effectively separate drugs and are marketed with different therapeutic indications. For example dextropropoxyphene (Darvon™, Lilly U.S.) is used as an analgesic which its enantiomer, levopropoxyphene (Novrad™, Lilly, U.S.) is used as an antitussive. Hutt et al. (1996) Drugs 52, suppl. 5:1–12.

In some cases, enantiomers can have opposite pharmacological effects. The (+) enantiomer of picenadol is an agonist at the opioid receptor while the (−) enantiomer acts as an antagonist at the same receptor. Powell et al. In: Wainer I W, Drager D E, editors, Drug Stereochemistry Analytical Methods and Pharmacology. New York, Marcel Dekker 1988: 245–70. The enantiomers of several of the chiral dihydropyridine calcium channel blockers also have opposite actions on the receptor. The S-enantiomers are potent activators at L-type voltage-dependant calcium channels whereas the R-enantiomers are antagonists. Triggle, D. J. Chirality, 1994: 6:58–62.

Several examples are known of single isomers whose pharmacological properties are so different from those of the racemate that the pure isomers have value for a new indication. Verpamil is able to inhibit the efflux of some cytotoxic drugs from certain multi drug-resistant tumor cell lines and could increase sensitivity of these cell lines to cytotoxic agents such as adriamycin. The use of verapamil for this purpose is limited by its cardiovascular effects which may be unwanted or even harmful. However, since the cardiovascular effects reside predominantly in the S-enantiomer, it may be possible to use pure R-verapamil to aid in the treatment of multi-drug resistant tumors at concentration that would be toxic if the racemate was used. Gottesman, M. M., Parton I Trend Pharmacol. Sci. 1988; 9:54–8; Plumb et al., Biochem. Pharmacol. 1990; 39:787–92.

The clinical value of using a pure enantiomer rather than a racemic drug may depend on other factors such as disease state, age, gender and genetic factors.

2.4 Chemistry and Pharmacokinetics of Tofisopam

Tofisopam is 1-(3,4-dimethoxy-phenyl)-4-methyl-5-ethyl-7,8-dimethoxy-5H-2,3-benzodiazepine which can be represented by the formula:

A synthesis of tofisopam is described in U.S. Pat. No. 3,736,315 to Korosi J., et al. Tofisopam is a 2,3 benzodiazepine that has been marketed in Europe as the racemic mixture under the name Grandaxin® as a minor tranquilizer. Tofisopam differs from the diazepam-like benzodiazepines in that the position of the nitrogen atoms in the ring structure are 2,3 instead of 1,4.

Tofisopam has a chiral center at carbon C-5 and therefore has two enantiomers. In addition, tofisopam can exist in two stable conformations based on the two configurations that can be assumed by the nitrogen containing benzodiazepine ring. The stereoselective binding to serum albumin of the two conformations has been reported to differ. Simongi, M. and Fitos, I., "Stereoselective Binding Of A 2,3 Benzodiazepine To Human Albumin," Biochemical Pharmacology 32:(12):1917–20 (1983).

Tofisopam (as a racemic mixture) has been used clinically as an anxiolytic in Europe for many years. Although there is structural similarity between tofisopam and classical 1,4 benzodiazepines (BDZ) such as diazepam, the difference in position of the nitrogen in the benzodiazepine ring in tofisopam confers pharmacological activity that is very different from classical BDZs.

Classical 1,4 BDZs, have specific high-affinity binding sites in the CNS. Mohler, H. and Okada, T., Benzodiazepine receptors: demonstration in the central nervous system, Science, (1977) 198:849–851; Squires, R. F. and Braestrap, C., Benzodiazepine receptors in rat brain, Nature 266:732–734, 1977. These specific binding sites are now known to be a subtype of the $GABA_A$ receptor. Tallman et al., GABA ergic modulation of benzodiazepine binding site sensitivity, Nature 1978:274:383–385; Tallman et al., Receptors for the age of anxiety: pharmacology of the benzodiazepines, Science 1980:207:274–281. Separate and distinct recognition sites associated with the $GABA_A$ receptor bind to several convulsant compounds such as picrotoxin and pentylenetetrazolin, Paul, S. M., GABA and Glycine in Psychopharmacology: The Fourth Generation of Progress, ed. Bloom and Kupfu p. 87–94, Raven Press Ltd., New York. Activation of the $GABA_A$ receptor by agonists results in an increase in Cl ion conductance via the receptor-gated ion channel or pore. The activation of Cl ion conductance results in hyperpolarization of the neuron and decreases its sensitivity to excitatory neuro-transmitters. This is the mechanism of action of the inhibitory neurotransmitter GABA and classical BDZ, such as diazepam exert their effect by this action.

Tofisopam does not bind to the benzodiazepine receptor in contrast to the clinically effective 1,4-BDZ. Tofisopam does not displace the binding of [$^3$H]-BDZs from their receptors (in vitro) or (in vivo) after administration via gastric tube and it does not displace inverse agonists (e.g. B carbolines)

at this receptor. Saano, V. and Urtti, A., *Pharmacol. Biochem. Behav.,* 17:367–369, 1982; Saano, V., *Pharmacol. Res. Commun.,* 14:971–981, 1982. However, tofisopam enhances the binding of BDZs to their receptors both (in vivo) and (in vitro) after both acute and chronic treatment. Saano, V. and Urtti, A., *Pharmacol. Biochem. Behav.* 17:367–369 (1982). Mennini et al., *Naunvn Schmiedaberg Arch. Pharmocol.,* 321:112–115, (1982). This effect is the result of an increase in the affinity of the receptor for the BDZ and not by an increase in the numbers of receptors. The ability of tofisopam to enhance the binding of BDZs is not due simply to pharmacokinetic factors since brain levels of diazepam and its metabolite desmethyldiazepam were unmodified by tofisopam. Pellow S. and File S E, *Neuroscience & Biobehavorial Reviews* 10:221–227, 1986.

The effects of tofisopam on dopamine systems are very different from those of classical 1,4 BDZs. At low doses tofisopam has been shown to have an agonist-like effect on brain dopaminergic systems. Szentendrei, T. et al., In: *Catecholamines and Stress: Recent Advances,* edited by E. Usdin, R. Kvetnanstig and I. J. Kopen, Amsterdam: Elsevier 1980, pp. 161–166. However, at higher doses tofisopam has a neuroleptic-like dopamine blocking effect. Pellow, s. and File S., *Neuroscience & Biobehavorial Review,* 10:221–227 (1986). It has been proposed that tofisopam induces a rapid supersensitization of dopamine receptors comparable to that observed after chronic treatment with haloperidol and at the same time increases the affinity of dopamine receptors for antagonists. Chopin, P. et al., J. Pharm. Pharmacol. 37:917919 (1985). This biphasic effect of tofisopam on dopamine systems is a marked contrast to those of classic 1,4-BDZ. These compounds act only as inhibitors of brain dopamineric systems and do not possess low-dose agonist-like effects.

2.5 Therapeutic Efficacy of Racemic Tofisopam

A large number of clinical studies have shown that tofisopam is an effective anxiolytic in humans. In a large multicenter study with 325 patients, tofisopam was given for 3 weeks, in dose ranges of 150–1300 mg/day. The drug was found to be an effective anxiolytic and did not have the sedative side effects that are observed with 1,4 BDZ. In fact the most significant adverse effect was a stimulant like side effect. Varady, G. et al., *Ther. Hung* 23:153–158, 1975. In an open study with 30 patients with mixed anxiety depression syndrome, tofisopam was found effective at an average dose of 158 mg/day. Molcan, J. V., *Aggressologie* 22D:23–24, 1980. Tofisopam was found effective at treating nervous tension, irritability and disturbed sleep patterns in patients with menopausal symptoms. Csillag, M. G., *Ther Hung* 23:164–169, 1975. In this study doses were 150–300 mg/day for a period of 3–4 weeks.

Tofisopam was found to be effective in treating 50 outpatients diagnosed with anxiety disorders. Some adverse side effects were noted including drowsiness and fatigue. This study also suggested that tofisopam may have a specific effect on the "fear" factor from the Hamilton anxiety scale which may be predictive of antiphobic effect. A double-blind study (doses not reported) comparing tofisopam with placebo was carried out over a 4 week period with 57 outpatients with anxiety and depression. Goldberg, H. L. and Finnerty, R. J., *Am. J. Psychiatry* 136:196–199 (1979). This study showed that tofisopam was significantly more effective than placebo at reducing symptomatology as measured by both the Hamilton Anxiety Scale and The Symptom Distress Checklist. Tofisopam was found to be unusually effective for patients who had prominent somatic concern on the Hamilton scale. However, twenty-one percent of the patients receiving tofisopam reported side effects during treatment compared to only ten percent of placebo recipients. One patient who received racemic tofisopam had an immediate and severe reaction which included excitement, confusion, syncope and dizziness which continued for more than 7 days. This patient had to be removed from the study. This is consistent with previous reports of that racemic tofisopam can cause adverse stimulatory effects. Varody et al., *Ther. Hung* 23:153–158, 1975. Other double-blind studies have confirmed the efficacy of tofisopam in the treatment of anxiety. Slodka, R. et al., *Ther. Hung.* 27:3–.7, 1979.

Tofisopam has also been shown to have a significant anxiolytic effect when given preoperatively and this effect was found to be superior to that of the classic 1,4 BDZ nitrazepam. Pakkanen, A. et al *Br. J. Anaesth.* 52:1009–1012, 1980. In another study of the use of tofisopam as a premedication, repeated oral doses of 100 mg were found to produce anxiolysis without sedation but with the undesirable side effect of stimulation. Kanto, J. et al., *Int. J. Clin. Pharmacol. Ther. Toxicol.* 20:309–313, 1982. Tofisopam has also been found effective in treating anxiety in patients with myasthenia gravis where the muscle relaxant effects of 1,4 BZDs can worsen the effects of the disease.

Tofisopam has also been found to improve cognitive performance in anxious patients without causing a psychomotor impairment. However, sleep disturbances were noted when tofisopam was administered in the evening and vigilance was increased. Maier, K., *Curr. Ther. Res.* 35:541–548 (1984).

In contrast to the 1,4 benzodiazepines, which all have anticonvulsant properties, Lister, R. G., *Neurosci. Biobehav. Rev.* 9:87–94, 1985, tofisopam has been reported to not have anticonvulsive, muscle relaxant or sedative effects. Gerevich, J. *Ther. Hungar.* 23:143–146, 1975. Petocz, L. and Kosoczky, I. *Ther. Hungar.* 23:143–138, 1975.

However, tofisopam does enhance the actions of diazepam, against convulsions, Briley, M., *Br. J. Pharmacol.* 82:300P, 1984; Mennini, T., Naugn-Schmiedeberg's *Arch. Pharmacol.* 321:112–115, 1982 and also enhances the action of diazepam against tremor. Saano, V. *Pharmacol. Biochem. Behav.* 17:367369, 1982; Saano, V. *Med. Biol.* 61:49–53, 1983. This action of tofisopam is specific to benzodiazepine anticonvulsants and was not found with phenytoin, sodium valproate or carbamazepine. Saano, V., *Med. Biol.* 64:201–206, 1986.

2.6 Tofisopam Enantiomers

The molecular structure and conformational properties of tofisopam have been determined by NMR, CD and x-ray crystallographic methods. Visy, J. and Simongi, M., *Chirality* 1:271–275 (1989). The 2,3 diazepine ring exists in two kinds of boat conformation. In the case of the major conformers (+)-R and (−)S, the ethyl group attached to the center of asymmetry C-5 has quasiequatorial orientation while in the minor conformer (−)R and (+)S this group is positioned quasiaxially. As a result, racemic tofisopam in solution contains four molecular species, i.e., two enantiomers each of which exists in two chiral conformations. The sign of optical rotation is reversed upon inversion of the diazepine ring. In crystal form tofisopam exists only as the major conformations, with levorotatory tofisopam being of the (S) absolute configuration. Toth, G. et al., *J. Heterocyclic Chem.* 20:709–713, 1983. Fogassy, E. et al., In: *Bio-Organic Heterocycles,* Van der Plas, H. C., Ötvös, L., Simongi, M., eds. Budapest Amsterdam: Akademia; Kiado-Elsevier, 1984, 229:233.

Fogassy et al. states that an abstract by Petocz et al. from a 1980 meeting describes pharmacological tests in mice which show different biological activity for the stereoisomers, including the observation that the activity of racemic tofisopam does not correspond with the sum of the activities of its enantiomers. Id. at 230. However, Fogassy et al. does not describe the biological assays or the specific results achieved by Petocz et al. Furthermore, a search of the prior art yielded no such abstract by Petocz et al. Thus, there is currently no indication that Petocz et al. exists or relates to R-tofisopam and its unexpected properties.

In addition the binding of tofisopam enantiomers to human serum albumin has been shown to be stereoselective and affected by the interconversion of conformations. Simonyi M. and Fitos, I. *Biochem Pharmacology* 32(12) :1917–1920 (1983).

2.7 Anxiety Disorders

The anxiety disorders are part of a heterogeneous group of psychiatric disorders that are characterized by their predominant symptom being that of anxiety. The Diagnostic and Statistical Manual of Mental Disorders, 4th Edition (DSMIV), published by The American Psychiatric Association, 1994, Washington, DC, lists twelve (12) different types of Anxiety Disorders. These are as follows: Panic Disorder without Agoraphobia; Panic Disorder with Agoraphobia; Agoraphobia Without History of Panic Disorder; Specific Phobia; Social Phobia; Obsessive Compulsive Disorder; Post-traumatic Stress Disorder; Acute Stress Disorder; Generalized Anxiety Disorder; Anxiety Disorder Due to a General Medical Condition; Substance Induced Anxiety Disorder; and Anxiety Disorder, Not Otherwise Specified.

Panic Disorder is characterized by the presence of recurrent unexpected panic attacks, followed by at least a month of persistent concern about having another panic attack, in addition to worry about the possible implications or consequences of the panic attacks, or a significant behavioral change related to the panic attack. A panic attack is a discreet period of intense fear or discomfort in which four (4) or more of the following symptoms develop abruptly and reach a peak within ten (10) minutes. The symptoms are palpitations, sweating, trembling, shortness of breath, feeling of choking, chest pain, nausea, feeling dizzy, derealization, depersonalization, fear of losing control, fear of dying, parasthesias, and chills or hot flashes.

The panic attack has a sudden onset and builds to a peak rapidly and is often accompanied by a sense of immediate danger or impending doom and an urge to escape. The panic attack differs from generalized anxiety in that the anxiety associated with the panic attack is intermittent and paroxysmal in nature and of greater severity. Panic attacks can occur in many different anxiety disorders, including Panic Disorder, Social Phobia, Specific Phobias, Post-Traumatic Stress Disorder and Acute Stress Disorder.

In Panic Disorder the frequency and severity of the panic attacks may vary widely. Some individuals may have frequent attacks, for example, daily or weekly, separated by periods without attacks. Other individuals may have only occasional panic attacks.

Panic Disorder is classified as with or without Agoraphobia. Agoraphobia is anxiety about being in situations in which escape would be difficult or even embarrassing, or in which the individual might not be able to obtain help.

Agoraphobia can also occur without a history of panic disorder. In this disorder, the focus of fear is on the occurrence of severe panic-like symptoms or embarrassment as a result of these symptoms, rather than full formal panic attacks. The majority of individuals who have Agoraphobia also have a current diagnosis or history of Panic Disorder. However, Agoraphobia without a history of Panic Disorder is reported to be as common as Panic Disorder with Agoraphobia.

Specific phobias are characterized by persistent and extreme fear of clearly defined, circumscribed objects or situations. Exposure to these particular objects or situations almost invariably produces an immediate anxiety, response, which may take the form of a panic attack. In children the anxiety may be expressed by tantrums, crying or clinging. The diagnostic criteria also require that the person recognize that the fear is excessive or unreasonable. In children this feature may be absent.

The essential feature of Social Phobia is marked and persistent fear of social situations in which embarrassment may occur. Exposure to this particular social situation will almost always produce an immediate anxiety response. This may take the form of a situationally predisposed panic attack. As in Specific Phobia, adolescents and adults with this disorder recognize that their fears are excessive or unreasonable but this is not the case with children. Individuals with Social Phobia have great concern about embarrassment and are often afraid that others will judge them to be anxious or even crazy or stupid. This may result in fear of public speaking because of the concern that others will notice that they are anxious or that they will be unable to speak articulately. Persons with this disorder may avoid eating, drinking or writing in public because of fear of embarrassment. Individuals with Social Phobia virtually always experience some symptoms of anxiety in the feared social situation and may have panic attacks, when exposed to the situation.

Obsessive Compulsive Disorder is a syndrome characterized by recurrent obsessions or compulsions that cause marked distress or take more than one hour a day or significantly interfere with the persons normal routine, occupational or academic functioning or usual social activities or relationships.

Obsessions are recurrent and persistent thoughts, impulses or images that are experienced at some point as intrusive and inappropriate and that cause marked anxiety and distress and are not simply excessive worries about real-life problems. The person attempts to ignore or suppress such thoughts, impulses or images or to neutralize them with some other thought or action and the person recognizes that the thought, impulses or images are a product of his or her own mind and not imposed from without.

Compulsions are repetitive behavior, such as handwashing or checking or mental acts such as counting or repeating words silently that the person feels driven to perform in response to an obsession or according to rules that must be applied rigidly. The person intends that these behaviors or mental acts will prevent distress or some dreaded event or situation however these behaviors or mental acts are not connected in a realistic way with what they are designed to neutralize or prevent or are clearly excessive.

Posttraumatic Stress Disorder (PTSD) is a syndrome characterized by clinically significant distress that results in disabling social and occupational dysfunction for periods of more than one month. The essential feature of PTSD is the development of characteristic symptoms following exposure to an extreme traumatic stressor involving direct personal experience of an event that involves actual or threatened death or serious injury, or other threat to one's physical integrity; or witnessing an event that involves death, injury, or a threat to the physical integrity of another person; or learning about the unexpected or violent death, serious injury, or threat of death or injury experienced by a family member or other close associate.

The patient's response to the event generally involves disorganized or agitated behavior. The characteristic symptoms resulting from the exposure to the extreme trauma include persistent re-experience of the traumatic event, persistent avoidance of stimuli associated with the trauma and numbing of general responsiveness, as well as persistent symptoms of increased arousal and anxiety not exhibited by the patient before the traumatic incident.

The traumatic event is most commonly re-experienced by way of recurrent and intrusive recollections of the events or recurrent distressing dreams of the event. PTSD can manifest itself chronically, defined as the presence of the full complement of symptoms for a period of 3 months or longer, or it may appear acutely, with each episode lasting less than 3 months. Occasionally, delayed-onset PTSD occurs, wherein at least 6 months have passed between the traumatic event and the onset of the above-described symptoms.

Furthermore, patients suffering from PTSD are at an increased risk for other debilitating psychiatric disorders, including Panic Disorder, Agoraphobia, Obsessive-Compulsive Disorder, Social Phobia, Major Depressive Disorder, and Substance Abuse. PTSD is also frequently associated with self-destructive, self-utilating, and impulsive behavior resulting in injury to the patient, such as head trauma or burns.

The essential feature of Acute Stress Disorder is the development of characteristic anxiety, dissociation and other symptoms that occurs within one on th after exposure to an extreme traumatic stressor. The types of stressors involved are similar to those involved in the development of PTSD. While experiencing the traumatic event or after the event the individual develops at least three of the following dissociative symptoms: a subjective sense of numbing, detachment or absence of emotional responsiveness; a reduction in awareness of his or her surroundings; derealization; depersonalization or dissociative amnesia. Following the trauma the event is persistently reexperienced and the individual displays marked avoidance of stimuli that may arouse recollections of the trauma and has marked symptoms of anxiety or increased arousal.

The essential feature of this syndrome is the development of dissociative symptoms along with symptoms similar to those of PTSD as a result of exposure to a traumatic event. Individuals with Acute Stress Disorder may neglect basic health and safety needs and are at increased risk of developing PTSD and Major Depression.

The essential feature of Generalized Anxiety Disorder is excessive anxiety and worry occurring on more days than not for a period of at least six months about a number of events or activities. The individual with Generalized Anxiety Disorder finds it difficult to control the worry and other symptoms occur which may include restlessness, irritability, muscle tension and disturbed sleep. Individuals with this disorder may not always identify the worries as "excessive" but they experience subjective distress, have difficulty controlling the worry and may experience related impairment in social, occupational or other important areas of functioning.

This disorder occurs in both children and adults and was formally called Overanxious Disorders of Childhood. Children with this disorder tend to worry excessively about their competence or the quality of their performance and they may be overly conforming, perfectionist and unsure of themselves.

Generalized Anxiety Disorder often co-occurs with Major Depressive Disorders or Dysthymic Disorders or other Anxiety Disorders or Substance-Related Disorder. Individuals with this disorder may often have associated somatic symptoms such as headaches or irritable bowel syndrome.

The essential feature of Anxiety Disorder Due to a General Medical Condition is clinically significant anxiety that is judged to be the direct physiological effect of a general medical condition. The symptoms may include generalized anxiety symptoms, panic attacks, or obsessions and compulsions. This syndrome is characterized not by the nature of the anxiety symptoms but by the judgment of the physician that they are the direct result of an underlying medical condition. Many examples of such medical condition are known to clinicians, such as thyroid disease, hypoglycemia, pulmonary embolism, cardiac arrhythmia, COPD, Vitamin $B_{12}$ deficiency and encephalitis.

Substance-induced Anxiety Disorder is characterized by prominent anxiety symptoms that are judged to be the direct physiological effect of a substance such as a drug of abuse, a medication or toxin exposure. The symptoms may include prominent anxiety, panic attacks, phobias or obsessions and compulsions and may occur during intoxication or during withdrawal. The symptoms are severe enough to cause clinically significant distress or impairment in social, occupational or other important areas of functioning. This condition is diagnosed only when the anxiety symptoms are in excess of those usually associated with the intoxication or withdrawal syndrome and are severe enough to warrant independent clinical attention. Many medications and drugs can cause anxiety symptoms during intoxication including: caffeine, cocaine, hallucinogens, anticholinergics, thyroid preparations, antipsychotic medications—and a variety of toxins. Anxiety symptoms can also occur in association with withdrawal from many classes of substances such as: alcohol, sedatives, anxiolytics or cocaine.

Anxiety Disorders Not Otherwise Specified includes disorders with prominent anxiety or phobic symptoms that do not meet criteria—for any specific Anxiety Disorder.

2.8 Treatment of Anxiety and Anxiety Disorders

Conventional treatment for anxiety and Anxiety Disorders has involved both psychological therapy such as psychotherapy and pharmacological intervention. Michelo, R. *J. Clin. Psychiatry;* 58(Suppl)3):30–32; Anxiety Disorders Chap. 109125 in *Psychopharmacology: The Fourth Generation of Progress,* eds. F. E. Bloom and D. J. Kupfer. Raven Press, Ltd., New York 1995.

Benzodiazepines remain one of the mainstays of the treatment armamentarium for anxiety and anxiety disorders either alone or in combination with other psychopharmacologic agents. Woods, J. H. et al. *Pharmacol Rev.* 1992:44:151–347, Shoder R. I. and Greenblatt D. J. *N. Engl. J. Med.* 1993:328:1398–1405. Hollister et al. *J. Clin. Psychopharmacol.* 1993; 13(suppl.):15–1695.

Benzodiazepines are frequently used in combination with antidepressants for the treatment of comorbied depression and anxiety. Research and clinical observation have shown that there is substantial overlap of these two distinct disorders. Depression and anxiety disorders are both common illnesses with lifetime prevalence of 8% and 15% respectively. In addition approximately 60% of patients with depression have some anxiety symptoms and from 20% to 30% of those patients have panic attacks. Lydiard R B *J. Clin. Psychiatry* 1991; 52(6, Suppl.):48–54. High rates of comorbied major depression are found in patients with anxiety disorders such as Agoraphobia (65%), Panic Disorders (69%) and Social Phobia (94%). Stein M B, Uhde T W, *Psychiatric Clin. North AM* 1988; 11(2):441–461.

In addition to the fact that many depressed patients have serious anxiety symptoms that require treatment, the presence of anxiety symptoms and especially a recent history of panic attacks was predictive of suicide risk in depressed patients. Fawcett J. *J. Clin. Psychiatry* 1988; 49 (10, Suppl) :7–8.

It is now recognized that an anxiety symptom and Anxiety Disorders should be aggressively treated whether they occur alone or in combination with other disorders such as depression. Keller, M. B. and Hantis, D. L. *J. Clin. Psychiatry* 1995; 56 (Suppl 16):22–29.

The symptoms of anxiety and Anxiety Disorders are often prolonged and therefore it may be advantageous to use controlled-release pharmaceutical preparations in the treatment of these conditions. All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time.

Due to the limitations of available psychotherapy and pharmaceutical intervention, alternate treatments for anxiety and Anxiety Disorders with greater efficacy and fewer adverse-side-effects are presently being sought.

3. SUMMARY OF THE INVENTION

The active compound of compositions and methods disclosed herein is the R enantiomer of tofisopam. The preparation of racemic Tofiosopam is described in U.S. Pat. No. 3,736,315, to Korosi J. et al. The chemical formula of R-tofisopam is R-1-(3,4-dimethoxyphenyl)-5-ethyl-7,8-dimethoxy-4-methyl-5H-2,3-benzodiazepine.

The invention encompasses the use of R-tofisopam or an R-tofisopam composition in the treatment of anxiety and anxiety disorders. Thus, one embodiment of the present invention relates to the treatment of anxiety and anxiety disorders by the administration of a therapeutically effective amount of R-tofisopam or a pharmaceutically acceptable salt thereof, which has unexpectedly better activity than its racemate and S-tofisopam.

The invention also encompasses the use of R-tofisopam or a tofisopam composition to prevent anxiety and anxiety disorders, such as by administration to an individual at risk of developing them, either alone or in combination with psychotherapy. Thus, the present invention also encompasses methods for preventing anxiety or anxiety disorders in a human by administering a therapeutically effective amount of R-tofisopam or a pharmaceutically acceptable salt thereof to said human.

The present invention also encompasses the use of R-tofisopam in conjunction with other known psychiatric medications such as tricyclic antidepressants, serotonin reuptake inhibitors, atypical antidepressants, monoamine oxidase inhibitors; 1,4 Benzodiazepine such as diazepam, lorazapam or alprazolam or major tranquilizers such as haloperidol or chlorpromazine.

The present invention further encompasses the use of R-tofisopam in conjunction with traditional psychotherapy to treat or prevent anxiety or anxiety disorders in a human by administering R-tofisopam or a pharmaceutically acceptable salt thereof to said human, before, during or after psychotherapeutic intervention.

The present invention encompasses the use of R-tofisopam to treat or prevent anxiety or anxiety disorders either alone or in conjunction with psychotherapy, in all potential human patient populations including men, women, children and the elderly.

The invention also encompasses a pharmaceutical composition which comprises an effective amount of R-tofisopam or a pharmaceutically acceptable salt thereof, substantially free of its S-enantiomer, together with one or more pharmaceutical carrier(s), diluent(s) and/or additives.

This invention further encompasses a controlled-release pharmaceutical composition adapted for the treatment of anxiety and Anxiety Disorders and methods of its administration.

3. FIGURES

FIGS. 3A and 3B are chromatograms of final preparations of the enantiomers of tofisopam.

4. DETAILED DESCRIPTION OF THE INVENTION

The present invention encompasses a method for treating anxiety or anxiety disorders in a human, which comprises administering to said human a therapeutically effective amount of the R enantiomer of tofisopam or a pharmaceutically acceptable salt thereof, substantially free of its S enantiomer, said amount being sufficient to alleviate said anxiety or anxiety disorder. In addition, the invention encompasses the treatment of anxiety with optically pure R-tofisopam or a pharmaceutically acceptable salt thereof, while reducing or avoiding the adverse effects associated with racemic tofisopam.

The present invention also encompasses a pharmaceutical composition for the treatment of a human suffering from anxiety or an anxiety disorder which comprises an amount of R-tofisopam or a pharmaceutically acceptable salt thereof substantially free of its S enantiomer, said amount being sufficient to alleviate said anxiety or anxiety disorder. In addition, the invention encompasses a pharmaceutical composition for the treatment of a human suffering from anxiety or an anxiety disorder comprising optically pure R-tofisopam or a pharmaceutically acceptable salt thereof, said composition being effective to alleviate said anxiety or anxiety disorder while reducing or avoiding the adverse effect associated with racemic tofisopam.

A further aspect of the present invention includes a method of preventing anxiety or Anxiety disorders in a human, while substantially reducing the concomitant liability of adverse effects associated with the administration of racemic tofisopam, which comprises administering to a human at risk for developing anxiety or an anxiety disorder, including anxiety that coexists with depression, either alone or in conjunction with psychotherapy, an amount of R-tofisopam or a pharmaceutically acceptable salt thereof, substantially free of its S-enantiomer, said amount being sufficient to alleviate said anxiety or anxiety disorder. In addition the invention encompasses the prevention of anxiety or anxiety disorders with optically pure R-tofisopam while reducing or avoiding the adverse effects associated with the administration of racemic tofisopam.

Furthermore, the present invention includes a composition for preventing anxiety or anxiety disorders in a human, which comprises an amount of R-tofisopam, or a pharmaceutically acceptable salt, thereof, substantially free of its S enantiomer, said amount being sufficient to alleviate said anxiety or anxiety disorder. In addition, the invention encompasses a composition for preventing or treating anxiety or anxiety disorders in a human, comprising optically pure R-tofisopam while reducing or avoiding adverse effects associated with the administration of racemic tofisopam.

The available racemic mixture of tofisopam (Grandaxin™) possesses antianxiety activity and provides therapy and reduction of symptoms of anxiety and anxiety disorders. However, this racemic mixture causes adverse effects including but not limited to excess stimulation, agitation and inability to sleep. The invention encompasses the use of the R enantiomer of tofisopam substantially free of its S enantiomer to result in diminished adverse effects and accordingly an improved therapeutic index.

The terms "R-tofisopam" or "optically pure R-tofisopam" refer to dextrorotatory R-tofisopam in solid form, substantially free of its levorotatory (S) enantiomer.

The term "substantially free of its S enantiomer" as used herein means that the composition contain at least 90% by weight of R-tofisopam and 10% by weight or less of S-tofisopam. In a preferred embodiment the term "substantially free of the (S) enantiomer" means that the composition contains at least 95% by weight of R-tofisopam and 5% or less of S-tofisopam. In a most preferred embodiment the term "substantially free of the S enantiomer" means that the composition contains at least 99% by weight of R-tofisopam and 1% or less of S-tofisopam. These percentages are based upon the total amount of tofisopam in the composition.

The chemical synthesis of the racemic mixture of tofisopam can be performed by the method described in U.S. Pat. No. 3,736,315, the disclosure of which is incorporated by reference. The R enantiomer of tofisopam may be obtained from its racemic mixture by resolution of the enantiomers using conventional means such as from an optically active resolving acid. See, for example, "Enantiomers, Racemates and Resolutions by J. A. Collet and S. H. Wilen, (Wileg-Interscience, New York, 1981); S. H. Wilen and J. A. Collet, Tetrahedron, 33, 2725 (1977) and "Stereochemistry of Carbon Compounds" by E. L. Eliel (McGrawHill, N.Y. 1962 and S. H. Wilen "Tables of Resolving Agents and Optical Resolution", E. L. Eliel, Ed. Univ. of Notre Dame Press, Notre Dame, Ind. 1972. See also T8th G. et al. J. Heterocgelic Chem; 20:709–713 (1983). Alternative methods of synthesis are disclosed in U.S. Pat. No. 4,423,044 to Korosi. This patent is incorporated herein by reference.

The magnitude of a prophylactic or therapeutic dose of the active ingredient (e.g., R-tofisopam) in the treatment or prevention of anxiety or anxiety disorders will vary with the severity of the patient's affliction and the route of administration. The dose and dose frequency will also vary according to the age, weight and response of the individual patient. In general, the recommended daily dose range for the conditions described herein lies within the range of from about 10 mg to about 1200 mg per day, generally divided equally into doses given one to four times a day. Preferably, a daily dose range should be between 50 mg and 600 mg per day, usually divided equally into a two to four times a day dosing. Most preferably, a daily dose range should be between 100 mg and 400 mg per day, usually divided equally into a two to four times a day dosing. It may be necessary to use dosages outside these ranges in some cases, and the treating physician will know how to increase, decrease or interrupt treatment based upon patient response. The various terms described above such as "therapeutically effective amount," are encompassed by the above-described dosage amounts and dose frequency schedule.

For use in treating or preventing anxiety or anxiety disorders, the physician will generally prescribe the period of treatment and frequency of dose of R-tofisopam on a patient-by-patient basis. In general, however, treatment or prevention of anxiety or anxiety disorders with R-tofisopam may be carried out for as long a period as necessary, either in a single, uninterrupted session or in discrete sessions. Most preferably, R-tofisopam therapy may be carried out for a period of 4 to 18 weeks. R-tofisopam may be administered before, along with, or after other psychoactive compounds, particularly those with antidepressant activity. Such compounds include tricyclic antidepressants such as amitriptyline, clomipramine, doxepin, imipramine, trimipramine, amoxapine, desipramine, maprotiline, nortriptyline, and protryptiline; serotonin-reuptake inhibitors such as racemic fluoxetine and enantiomers, fluvoxamine, paroxetine, sertraline, and (±)-venlafaxine; atypical antidepressants such as bupropion, nefazodone, and trazodone; and other monoamine oxidase inhibitors, such as phenelzine, tranylcypromine, and (–)-selgiline, either singly or in combination. In particular, the present invention encompasses the use of tofisopam in conjunction with other known psychoactive medications.

R-tofisopam may also be administered before, along with, or after traditional psychotherapy. Thus, R-tofisopam may be utilized in accordance with the present invention as an adjunct to conventional behavioral therapy or psychotherapy.

Any suitable route of administration may be employed for providing the patient with an effective dosage of R-tofisopam. For example, oral, rectal, parenteral, transdermal, subcutaneous, sublingual, intranasal, intramuscular, intrathecal and the like may be employed as appropriate. Dosage forms include tablets, coated tablets, caplets, capsules (e.g. hard gelatin capsules), troches, dragees, dispersions, suspensions, solutions, patches and the like, including sustained release formulations well known in the art. See, e.g. *Introduction to Pharmaceutical Dosage Forms,* 1985, Ansel, H. C., Lea and Febiger, Philadelphia, Pa.; *Remington's Pharmaceutical Sciences,* 1995, Mack Publ. Co., Easton, Pa.

The pharmaceutical compositions of the present invention comprise R-tofisopam as the active ingredient or a pharmaceutically acceptable salt thereof, and may also contain a pharmaceutically acceptable carrier and optionally other therapeutic ingredients. The term "pharmaceutically acceptable salt" refers to salts prepared from pharmaceutically acceptable non-toxic acids including inorganic acids and organic acids.

Since the compound of the present invention is basic, salts may be prepared from pharmaceutically acceptable nontoxic acids including inorganic and organic acids. Such acids include malic, acetic, benzene-sulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic; nitric, pamoic, pantothenic, phosphoric, succinic, sulfuric, tartaric, p-toluenesulfonic acid and the like. Particularly preferred are hydrobromic, hydrochloric, maleic, phosphoric, and sulfuric acids.

The compositions include compositions suitable for oral, rectal, transdermal, sublingual, and parenteral administration (including subcutaneous, intramuscular, intrathecal and intravenous), although the most suitable route in any given case will depend on the nature and severity of the condition being treated. The most preferred route of administration of the present invention is the oral route. The composition may be conveniently presented in unit dosage form and prepared by any of the methods well-known in the art of pharmacy.

In the case where an oral composition is employed, a suitable dosage range for use is, e.g., from about 10 mg to about 1200 mg per day, generally divided equally into a one to four times a day dosing, preferably from about 50 mg to about 600 mg per day, generally divided equally into a two to four times a day dosing and most preferably from about 100 mg to about 400 mg per day, generally divided equally into a two to four times a day dosing. Patients may be upward titrated from below to within this dose range to achieve satisfactory control or prevention of symptoms as appropriate.

In practical use, R-tofisopam can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous injections or infusions). In preparing the compositions for oral dosage form, any of the usual pharmaceutical media may be employed, for example, water, glycols, oils, alcohols, flavoring agents, preservatives, coloring agents and the like in the case of oral liquid preparations, for example, suspensions, elixirs and solutions; or aerosols; or carriers such as starches, sugars, microcrystalline cellulose, stabilizers, diluents, granulating agents, lubricants, binders, fillers, disintegrating agents and the like in the case of oral solid preparations such as, powders, capsules and tablets, with the solid oral preparations being preferred over the liquid preparations. The preferred solid oral preparation is tablets. The most preferred solid oral preparation is coated tablets. Because of their ease of administration tablets and capsules represent the most advantageous oral dosage unit form, in which case solid pharmaceutical carriers are obviously employed. If desired, tablets may be coated by standard aqueous or nonaqueous techniques.

The pharmaceutical compositions of the present invention may also be formulated so as to provide slow or controlled release of the active ingredient therein using, for example, hydropropylmethyl cellulose in varying proportions to provide the desired release profile, other polymer matrices, gels, permeable membranes, osmotic systems, multilayer coatings, microparticles, liposomes and/or microspheres.

In general, a controlled-release preparation is a pharmaceutical composition capable of releasing the active ingredient at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations.

U.S. Pat. No. 5,674,533 discloses controlled-release pharmaceutical compositions in liquid dosage forms for the administration of moguisteine, a potent peripheral antitussive.

U.S. Pat. No. 5,059,595 describes the controlled-release of active agents by the use of a gastro-resistant tablet for the therapy of organic mental disturbances.

U.S. Pat. No. 5,591,767 describes a liquid reservoir transdermal patch for the controlled administration of ketorolac, a non-steroidal anti-inflammatory agent with potent analgesic properties.

U.S. Pat. No. 5,120,548 discloses a controlled-release drug delivery device comprised of swellable polymers.

U.S. Pat. No. 5,073,543 describes controlled-release formulations containing a trophic factor entrapped by a ganglioside-liposome vehicle.

U.S. Pat. No. 5,639,476 discloses a stable solid controlled-release formulation having a coating derived from an aqueous dispersion of a hydrophobic acrylic polymer.

Biodegradable microparticles are known for use in controlled-release formulations.

U.S. Pat. No. 5,354,566 discloses a controlled-release powder that contains the active ingredient.

U.S. Pat. No. 5,733,566, describes the use of polymeric microparticles that release antiparasitic compositions. The use of R-tofisopam in a controlled-release formulation has not been previously disclosed.

The controlled-release of the active ingredient may be stimulated by various inducers, for example pH, temperature, enzymes, water, or other physiological conditions or compounds. Various mechanisms of drug release exist. For example, in one embodiment, the controlled-release component may swell and form porous openings large enough to release the active ingredient after administration to a patient. The term "controlled-release component" in the context of the present invention is defined herein as a compound or compounds, such as polymers, polymer matrices, gels, permeable membranes, liposomes and/or microspheres, that facilitate the controlled-release of the active ingredient (i.e., R-tofisopam) in the pharmaceutical composition. In another embodiment, the controlled-release component is biodegradable, induced by exposure to the aqueous environment, pH, temperature, or enzymes in the body. In another embodiment, sol-gels may be used, wherein the active ingredient is incorporated into a sol-gel matrix that is a solid at room temperature. This matrix is implanted into a patient, preferably a mammal, having a body temperature high enough to induce gel formation of the sol-gel matrix, thereby releasing the active ingredient into the patient.

Pharmaceutical stabilizers may also be used to stabilize compositions containing tofisopam or salts thereof; acceptable stabilizers include but are not limited to L-cysteine hydrochloride, glycine hydrochloride, malic acid, sodium metabisulfite, citric acid, tartaric acid and L-cysteine dihydrochloride.

Pharmaceutical compositions of the present invention suitable for oral administration may be presented as discrete units such as capsules, cachets, or tablets or aerosol sprays, each containing a predetermined amount of the active ingredient, as a powder or granules or as a solution or a suspension in an aqueous liquid, a non-aqueous liquid, an oil-in-water emulsion, or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine the active ingredient in a free-flowing form such as powder or granules, optionally mixed with one or more of a binder, filler, stabilizer, lubricant, inert diluent, and/or surface active or dispersing agent. Molded tablets may be made by molding in a suitable machine a mixture of the powdered compound moistened with an inert liquid diluent. Desirably, each tablet contains from about 10 mg to about 100 mg of the active ingredient, and each cachet or capsule contains from about 10 mg to about 200 mg of the active ingredient. In a preferred embodiment, the tablet, cachet or capsule contains one of four dosages: about 10 mg, about 50 mg, about 100 mg, and about 150 mg of active ingredient.

For example, tablets containing 20 mg of active agent (e.g., optically pure R-tofisopam may be prepared in a manner known in the art. The composition of one such tablet is as follows:

| Tablets | |
| --- | --- |
| Formula | Quantity per Tablet in mg. |
| Active ingredient | 20.0 |
| Magnesium stearate | 1.0 |
| Stearin | 1.0 |
| Talc | 2.0 |
| Gelatin | 3.5 |
| Maize starch | 20.5 |
| Lactose | 122.0 |
| Microcrystalline cellulose | 10.0 |

Several animal models are suitable for measuring the relative activities of the optically pure R and S enantiomers of tofisopam, as well as racemic tofisopam, in treating anxiety in humans. Evaluation of the compounds is based on their relative potencies in a test designed to measure the anxiety generated by a novel situation. In the "Elevated Plus-maze" Test, anxiety is generated by placing the animals on the elevated open arm of an apparatus in the shape of a cross (or "plus") with two open and two enclosed arms. The test animal has free access to all arms. Anxiolytic activity is determined by the percentage of time that the animals spend on the open arms and the percentage of all entries made into the open arms. This test has been validated behaviorally and physiologically in the rat and in the mouse. Pellow, S. et al. (1985) *J. Neurosci. Methods,* 14, 149–167; Lister, R. G. (1987) *Psychopharmacology,* 92, 180–185.

Other assays for anxiolytic activity can also be used and are known to those with skill in the art. Examples of other assays are the Geller-Seifter Test, the Vogel test and the Social Interaction Test. Still another assay is the head-twitch response assay (Moser, P. C., "The Effect of Novel Axiolytics on the Head-Twitch Response in Mice," *British J. Pharmacol. Suppl.* 99:248P (1990)).

Assays for monitoring the blocking of dopamine receptors are known in the art and are useful according to this invention (e.g., Bunzow, J. R., et al., "Cloning and Expression of Rat D2 Dopamine Receptor cDNA," *Nature* 336:783–787 (1988); Grandy, et al., "Cloning of the cDNA and Gene for a Human D2 Dopamine Receptor," *PNAS U.S.A.* 86:9762–9766 (1989); Hayes, G., et al., "Structural Subtypes of the Dopamine D2 receptor are Functionally Distinct: Expression of the Clone $D_{2A}$ and $D_{2B}$ Subtypes in a Heterologous Cell Line," *Mol. Endocrin.* 6:920–926 (1992). Preliminary results suggest that R-tofisopam cannot manifest side effects related to binding to the dopamine ($D_{2L}$) receptor.

Throughout this specification and claims, the word "comprise," or variations such as "comprises" or "comprising," will be understood to imply the inclusion of a stated integer or group of integers but not the exclusion of any other integer or group of integers.

In order that this invention be more fully understood, the following examples are set forth. These examples are for the purpose of illustration only and are not to be construed as limiting the scope of the invention in any way.

5. EXAMPLES

5.1 Resolution of Tofisopam Enantiomers

Figure 1:
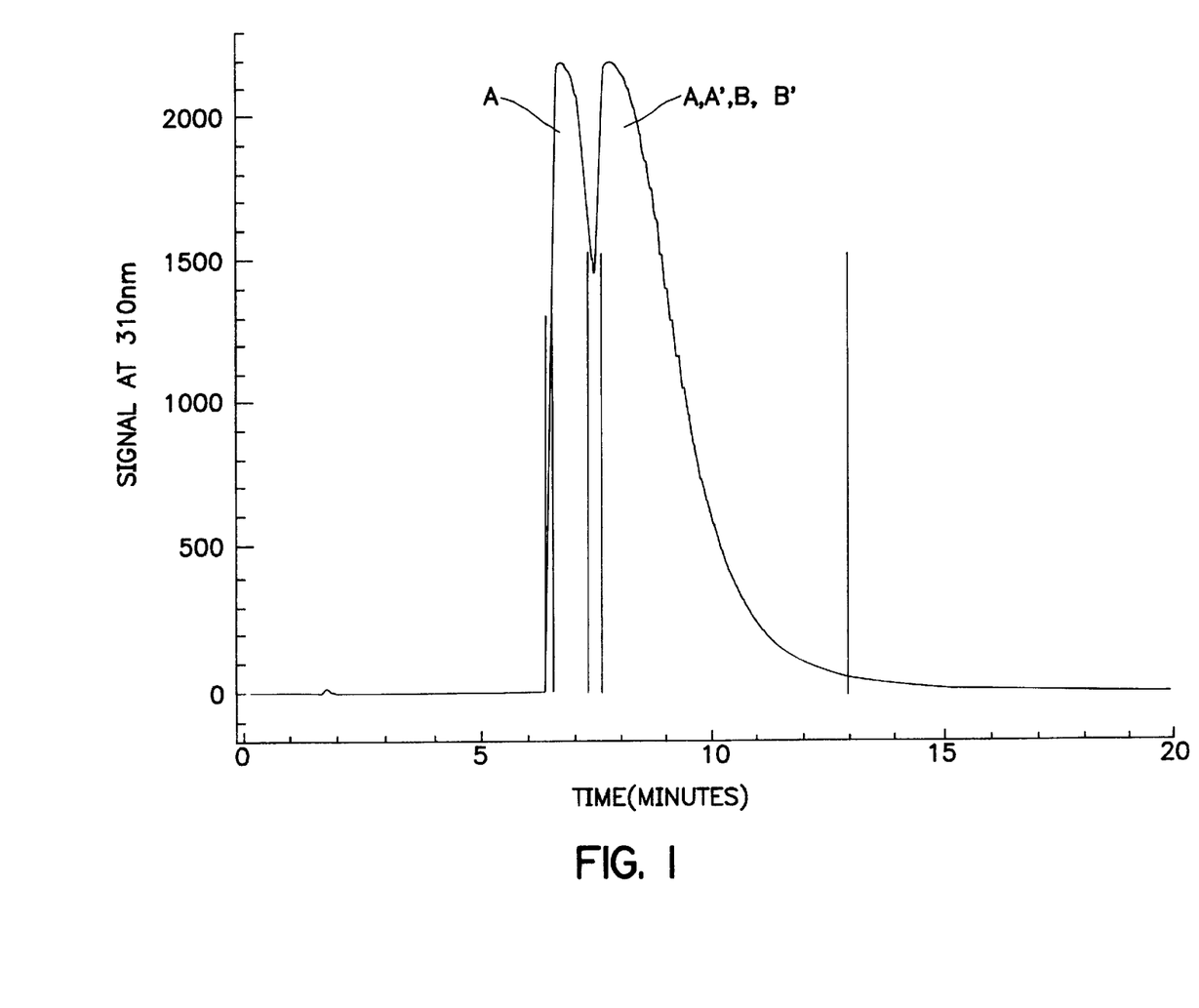
FIG. 1 is a chromatogram showing the preparative resolution of R-tofisopam using a Chirobiotic V column. The first peak, fraction 1, contains R(+)-tofisopam, which partially converts to R(−)-tofisopam and subsequently exists in a 80/20 (R+/R−) equilibrium. The second peak, fraction 2, contains R(−)-tofisopam, S(+/−)-tofisopam, and residual R(+)-tofisopam.

The enantiomers of tofisopam were resolved by chiral chromatography. For example, tofisopam (42.8 mg dissolved in acetonitrile) was loaded onto a Chirobiotic V column (ASTEC, Whippany, N.J.). Elution of the compounds with MTBE/ACN 90/10 (v/v), 40 ml/min, was monitored at 310 nm, 2 mm path. The R(+) enantiomer was the first compound to elute from the column. See FIG. 1, fraction 1. The R(+) enantiomer was collected, dried and stored for use in biological assays. R(−)-tofisopam ("A'"), S(−/+) tofisopam ("B" and "B'"), and residual R(+)-tofisopam ("A") co-eluted and was collected in a subsequent fraction (e.g., FIG. 1, fraction 2). Approximately 20% of the R(+)-tofisopam in fraction 1 is converted into R(−)-tofisopam if left in solution for 24 hours. A 80/20 stable equilibrium (R+/R−) was observed between the two conformers in MTBE/ACN (90/10) solution at room temperature.

Figure 2:
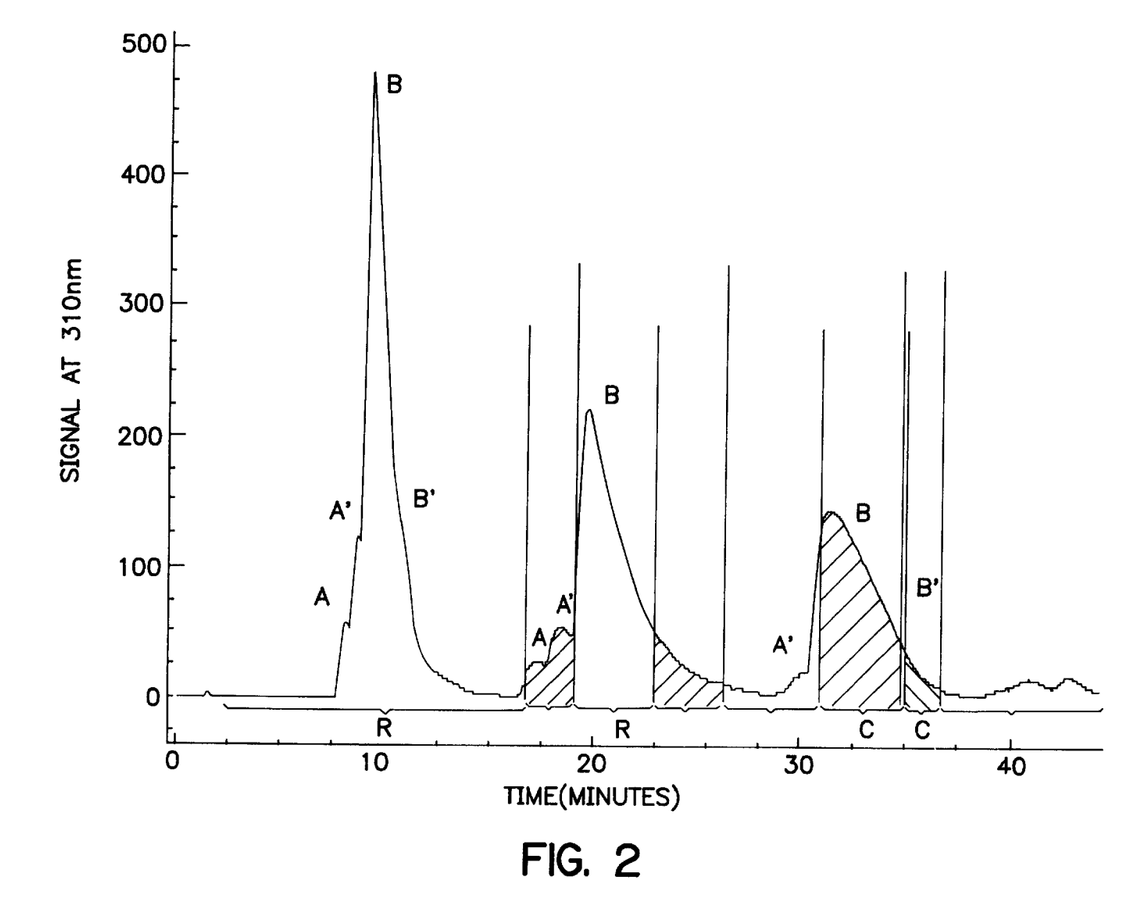
FIG. 2 is a chromatogram showing a preparative resolution of S-tofisopam by using a Chirobiotic V column and the shave recycling technique. The letter "R" indicates the fractions recycled. The letter "C" indicates the fractions collected. The material that eluted as indicated under the word After the third recycle, S-tofisopam (peaks B and B') was collected for analytical and biological assays.

The S(−) enantiomer was isolated from fraction 2 by the following protocol. Fraction 2 was dried, re-dissolved in 1 ml of acetonitrile and loaded onto a Chirobiotic V column. Peak B and B' was shave recycled over a Chirobiotic V column two more times (MTBE/ACN 90/10 (v/v), 40 ml/min monitored at 310 nm, 2 mm path). See, e.g., FIG. 2, Recycles 1–3. A peak containing S(−)-tofisopam was collected from the third recycle, dried and stored for use in biological assays (FIG. 2, peak B, third recycle).

Figure 3A:
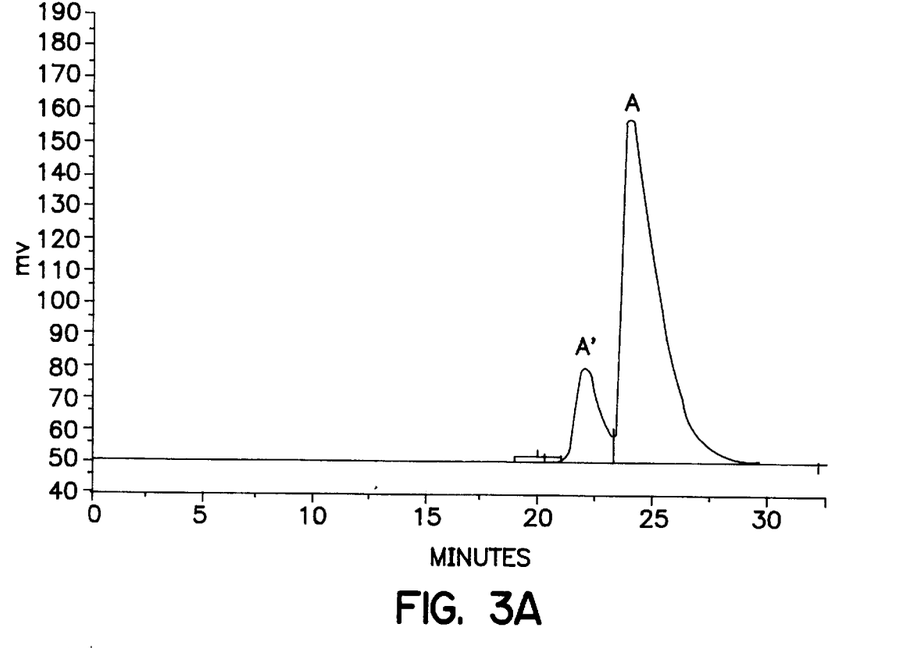
FIG. 3A shows a final preparation of R-tofisopam, which contains R(+)-tofisopam (Peak A) and R(−)-tofisopam (Peak A').
Figure 3B:
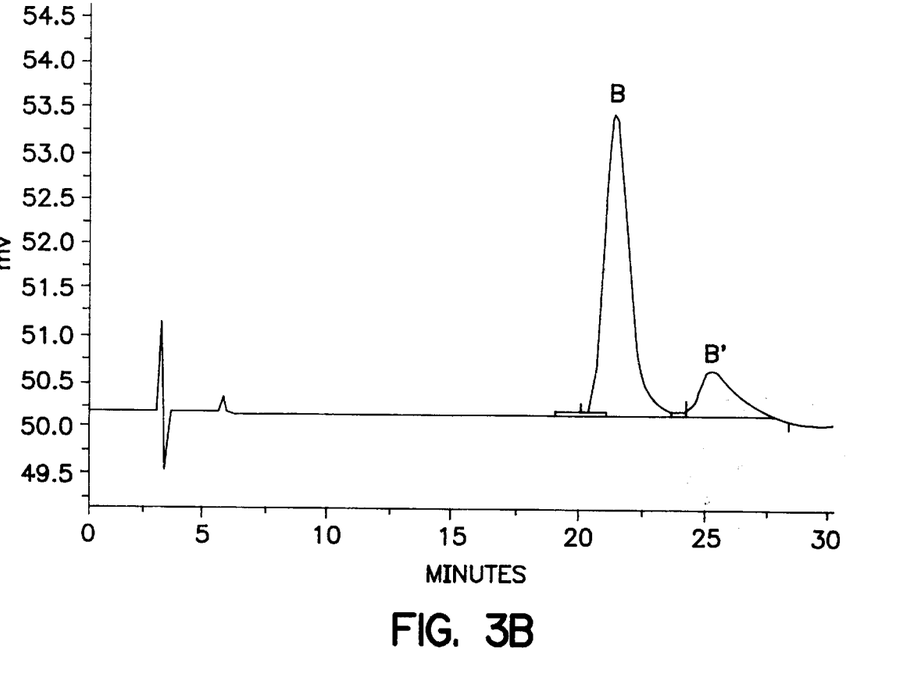
FIG. 3B shows a final preparation of S-tofisopam, which contains S(−)-tofisopam (Peak B) and S(+)-tofisopam (Peak B').

Analytical evaluations of the starting material, and final preparations of R- and S-tofisopam were performed by using Chiral Tech OD GH060 columns (Daicel) (Hexane/IPA 90/10, 25° C., detection at 310 nm). See FIG. 3*a* and 3*b.* The final preparation of R-tofisopam was 98%+ pure by analytical chromatography. The final preparation of S-tofisopam was 95%+ pure by analytical chromotography.

5.2 Assay for Anxiolytic Activity a. Test Substances

Dry preparations of tofisopam, R-tofisopam or S-tofisopam were dissolved in 2% Tween 80/5% DMSO for oral administration in a blind assay. Diazepam (Sigma, U.S.A.) was similarly dissolved in DMSO (Merck, Germany), distilled water and Tween 80 (Wako Pure Industries, Ltd., Japan).

b. Animals

Male Long Evans rats provided by animal breeding center of MDS Panlabs Taiwan, Ltd., were used. Space allocation for animals was as follows: 45×23×15 cm for 6 rats. Rats were housed in APEC® (Allentown Gaging, Allentown, N.J. 08501, U.S.A.) cages in a positive pressure isolator (NuAire®, Mode: Nu-605, airflow velocity 50±5 ft/min, HEPA Filter). All animals were maintained in a controlled temperature (22° C.–24° C.) and humidity (60%–80%) environment with 12 hours light dark cycles for at least one week in MDS Panlabs Taiwan laboratory prior to being used. Free access to standard lab chow for rats (Fwusow Industry Co., Limited, Taiwan) and tap water was granted. All aspects of this work including housing, experimentation and disposal of animals were performed in general accordance with the International Guiding Principles for Biomedical Research Involving Animals (CIOMS Publication No. ISBN 92 90360194, 1985).

c. Assay Protocol

Benzodiazepines, such as diazepam, have been shown to potentiate head-twitches induced by the direct 5-hydroxytryptamine (5-HT) receptor agonist 5-methoxy-N, N-dimethyltryptamine (5-MeODMT). Moser, P. C., "The Effect of Novel Axiolytics on the Head-Twitch Response in Mice," *British J. Pharmacol. Suppl.* 99:248P (1990). Based on those assays, test substances were administered orally to the rats one hour before interperitoneal injection of 3 mg/kg 5-MeODMT. The number of head-twitches over a 1–5 minute period post injection were recorded (Table 1).

TABLE 1

| Compound | Route | Dose | No. | Head Twitch | Score |
|---|---|---|---|---|---|
| Vehicle | PO | 10 ml/kg | 1 | 0 | 0 |
| (2% Tween 80/ | PO | 10 ml/kg | 2 | 0 | |
| 5% DMSO/DW) | PO | 10 ml/kg | 3 | 0 | |
| R-tofisopam | PO | 30 mg/kg | 1 | 0 | 1 |
| | PO | 30 mg/kg | 2 | 2 | |
| | PO | 30 mg/kg | 3 | 1 | |
| S-tofisopam | PO | 30 mg/kg | 1 | 0 | 0 |
| | PO | 30 mg/kg | 2 | 0 | |
| | PO | 30 mg/kg | 3 | 0 | |
| tofisopam | PO | 30 mg/kg | 1 | 0 | 0 |
| | PO | 30 mg/kg | 2 | 0 | |
| | PO | 30 mg/kg | 3 | 0 | |
| Diazepam | PO | 10 mg/kg | 1 | 5 | 2 |
| | PO | 10 mg/kg | 2 | 1 | |
| | PO | 10 mg/kg | 3 | 9 | |

With the administration of higher test doses, the number of head twitches observed in rats administered with tofisopam and R-tofisopam will increase in a dose-dependent manner.

The embodiments of the present invention described above are intended to be merely exemplary and those skilled in the art will recognize, or be able to ascertain using no more than routine experimentation, numerous equivalents to the specific procedures described herein. All such equivalents are considered to be within the scope of the present invention and are covered by the following claims. Other embodiments are within the following claims.

The contents of all references described herein are hereby incorporated by reference.

What is claimed is:

1. A method of treating anxiety or Anxiety Disorders in a human, which comprises administering to a human in need of treatment for anxiety or Anxiety Disorder a therapeutically effective amount of R-tofisopam, or a pharmaceutically acceptable salt thereof, substantially free of its S enantiomer.

2. A method of preventing anxiety or an Anxiety Disorder in a human at risk for developing anxiety or an Anxiety Disorder, which comprises administering to said human in need of prevention of anxiety or an Anxiety Disorder an amount of R-tofisopam, or a pharmaceutically acceptable salt thereof, substantially free of its S enantiomer, said amount being sufficient to prevent said anxiety or Anxiety Disorder.

3. A method of claims 1 or 2 wherein R-tofisopam is administered by intravenous infusion, transdermal delivery or orally as a tablet, a capsule or a liquid suspension.

4. The method of claim 3 wherein the amount of R-tofisopam or a pharmaceutically acceptable salt thereof administered is from about 10 mg to about 1200 mg.

5. The method of claim 4 wherein the amount administered is from about 50 to about 600 mg.

6. The method of claim 5 wherein the amount administered is from about 100 to about 400 mg.

7. The method of claim 4 wherein the said amount is administered in one to four unit doses per day.

8. The method of claim 7 wherein the said amount is administered in one to two unit doses per day.

9. The method of claims 1 or 2 wherein the amount of R-tofisopam or a pharmaceutically acceptable salt thereof is greater then approximately 90% by weight of the total weight of tofisopam.

10. The method of claims 1 or 2 wherein the amount of said R-tofisopam or a pharmaceutically acceptable salt thereof substantially free of its S enantiomer is administered together with a pharmaceutically acceptable carrier.

11. The method of claims 1 or 2 further comprising treating said human with psychotherapy designed to alleviate, minimize or prevent anxiety or anxiety disorders.

12. The method of claim 1 or claim 2 further comprising treating said human with an antidepressant.

13. The method of claim 12 wherein the antidepressant is a tricyclic antidepressant.

14. The method of claim 13 wherein the tricyclic antidepressant is selected from the group consisting of amitriptyline, clomipramine, doxepin, imipramine, (+)-trimipramine, amoxapine, desipramine, maprotiline, nortriptyline, and protryptiline.

15. The method of claim 12 wherein the antidepressant is selected from the group consisting of fluoxetine, fluvoxamine, paroxetine, sertraline, (±)-venlafaxine, bupropion, nefazodone, trazodone, phenelzine, tranylcypromine, (−)-selegiline and moclobemide.

16. The method of claims 1 or 2 further comprising treating said human with 1,4 benzodiazepine.

17. The method of claim 16 wherein the 1,4 benzodiazepine is selected from the group consisting of diazepam, lorazepam and alprasolam.

18. The method of claim 1 or 2 further comprising treating said human with an antipsychotic medication.

19. The method of claims 1 or 2 wherein R-tofisopam is administered in a sustained or controlled release formulation.

20. The method of claim 1 or 2 wherein said administration is made one to four times per day.

21. The method of claim 1 or 2 wherein the Anxiety Disorder is Panic Disorder without Agoraphobia.

22. The method of claim 1 or 2 wherein the Anxiety Disorder is Panic Disorder with Agoraphobia.

23. The method of claim 1 or 2 wherein the anxiety disorder is Agoraphobia Without History of Panic Disorder.

24. The method of claim 1 or 2 wherein the anxiety disorder is a Specific Phobia.

25. The method of claim 1 or 2 wherein the anxiety disorder is Social Phobia.

26. The method of claim 1 or 2 wherein the anxiety disorder is Obsessive Compulsive Disorder.

27. The method of claim 1 or 2 wherein the anxiety disorder is a Post-traumatic Stress Disorder.

28. The method of claim 1 or 2 wherein the anxiety disorder is an Acute Stress Disorder.

29. The method of claim 1 or 2 wherein the anxiety disorder is Generalized Anxiety Disorder.

30. The method of claim 1 or 2 wherein the anxiety disorder is Anxiety Disorder Due to a General Medical condition.

31. The method of claim 1 or 2 wherein the anxiety disorder is Substance-Induced Anxiety Disorder.

32. The method of claim 1 or 2 wherein the anxiety disorder is Anxiety Disorder Not Otherwise Specified.

33. The method of claim 1 or 2 wherein the anxiety is coexistant with depression.

34. The method of claim 1 or 2 wherein said therapeutically effective amount of R-tofisopam is insufficient to cause the adverse effects associated with the use of racemic tofisopam.

35. A pharmaceutical composition which comprises an effective amount of R-tofisopam or a pharmaceutically acceptable salt thereof; substantially free of its S enantiomer, together with one or more pharmaceutical carrier(s), diluent (s) and/or additives.

36. The composition of claim 35, wherein said composition is a controlled-release pharmaceutical composition.

37. The composition of claim 36, wherein the composition is adapted for the treatment of anxiety and Anxiety Disorders.

* * * * *

UNITED STATES PATENT AND TRADEMARK OFFICE
CERTIFICATE OF CORRECTION

PATENT NO : 6,080,736

DATED : June 27, 2000

INVENTION(S) : METHODS AND COMPOSITIONS FOR TREATING AND PREVENTING ANXIETY AND ANXIETY DISORDERS USING OPTICALLY PURE (R) TOFISOPAM

It is certified that error appears in the above-identified patent and that said Letters Patent are hereby corrected as shown below:

```
     Column 1, line 63, "molecules" should be --molecule's--;
     Column 6, line 59, "neuro-transmitters" should be
--neurotransmitters--;
     Column 7, line 7, "Naunvn" should be --Naunyn--;
     Column 7, line 23, "s." should be --S.--;
     Column 7, line 44, and Column 8, line 10, "Hung" should be
--Hung.--;
     Column 8, line 8, remove "of";
     Column 8, line 12, "Slodka" should be --Sladka-- and
"27:3-.7" should be --27:3-7--;
     Column 8, line 16, "et al" should be --et al.--;
     Column 10, line 11, remove the comma after "anxiety";
     Column 10, line 34, remove the comma after "attacks";
     Column 10, line 39, "persons" should be --person's--;
     Column 10, line 61, "Posttraumatic" should be
--Post-traumatic--;
     Column 11, line 29, "self-utilating," should be
--self-mutilating--;
     Column 11, line 34, "on th" should be --month--;
     Column 12, line 48, "Suppl)3" should be -Suppl 3--;
     Column 12, line 61, and Column 13, line 3 "comorbied" should
be --comorbid-;
     Column 13, line 31, "adverse-side-effects" should be
--adverse side-effects--;
     Column 13, line 34, "3." should be -2.9-;
     Column 15, line 4, "disorders" should be --Disorders--;
     Column 15, line 41, "contain" should be --contains--;
```

UNITED STATES PATENT AND TRADEMARK OFFICE
CERTIFICATE OF CORRECTION

PATENT NO : 6,080,736
DATED : June 27, 2000
INVENTION(S) : METHODS AND COMPOSITIONS FOR TREATING AND PREVENTING ANXIETY AND ANXIETY DISORDERS USING OPTICALLY PURE (R) TOFISOPAM It is certified that error appears in the above-identified patent and that said Letters Patent are hereby corrected as shown below:

```
Column 15, line 64, "T8th G." should be --G. Toth--;
Column 15, line 65, "erocgelic" should be --erocyclic--;
Column 17, line 10, "mucic;" should be --mucic,--;
Column 22, claim 9, "then" should be --than--;
Column 23-24, claims 23-32, "anxiety disorder" should be
--Anxiety Disorder--.
```

Signed and Sealed this

Twenty-fourth Day of April, 2001

Attest:

NICHOLAS P. GODICI

*Attesting Officer*  *Acting Director of the United States Patent and Trademark Office*